(12) United States Patent
Nock et al.

(10) Patent No.: US 6,716,168 B2
(45) Date of Patent: Apr. 6, 2004

(54) ULTRASOUND DRUG DELIVERY ENHANCEMENT AND IMAGING SYSTEMS AND METHODS

(75) Inventors: Levin Nock, Bellevue, WA (US); Ashutosh Chilkoti, Durham, NC (US); Kathryn R. Nightingale, Durham, NC (US); Gregg E. Trahey, Hillsborough, NC (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 0 days.

(21) Appl. No.: 10/136,610

(22) Filed: Apr. 30, 2002

(65) Prior Publication Data

US 2003/0204141 A1 Oct. 30, 2003

(51) Int. Cl.$^7$ .............................................. A61B 8/00
(52) U.S. Cl. .................... 600/439; 604/890.1; 601/2
(58) Field of Search .................... 600/437, 439, 600/458, 466, 407; 601/1, 2, 3; 606/128; 604/22, 20, 458, 407, 96.01, 101.01–101.05, 890.1

(56) References Cited

U.S. PATENT DOCUMENTS

| | | |
|---|---|---|
| 5,307,816 A | 5/1994 | Hashimoto et al. |
| 5,421,816 A | 6/1995 | Lipkovker |
| 5,490,840 A | 2/1996 | Uzgiris et al. |
| 5,523,058 A | 6/1996 | Umemura et al. |
| 5,558,092 A * | 9/1996 | Unger et al. ............... 600/439 |
| 6,113,558 A * | 9/2000 | Rosenschein et al. .......... 601/2 |
| 6,164,440 A | 12/2000 | Van Bree |
| 6,296,619 B1 * | 10/2001 | Brisken et al. ............... 604/22 |
| 6,428,477 B1 * | 8/2002 | Mason ....................... 600/437 |

OTHER PUBLICATIONS

"Acoustic Radiation Force Impulse Imaging: In Vivo Demonstration of Clinical Feasibility," by Kathryn Nightingale, Mary Scott Soo, Roger Nightingale, and Gregg Trahey; Oct. 24, 2001.

"Analysis of Clot Formation with Acoustic Radiation Force," by Francesco Viola, Diane M. Longo, Michael Be. Lawrence, and William F. Walker (Dept. of Biomedical Engineering, University of Virginia), Proceedings of SPIE vol. 4687 (2002).

* cited by examiner

Primary Examiner—Marvin M. Lateef
Assistant Examiner—Ruby Jain

(57) ABSTRACT

A method and system for both enhancing drug uptake by application of therapeutic transmissions of acoustic energy and imaging a region for applied therapy with a same transducer and ultrasound system. An ultrasonic image of a field of view is generated while localized delivery of a drug is enhanced with ultrasound energy. Using the same transducer and ultrasound system reduces costs and increases system availability for a broader range of medical practitioners. For example, a single linear array of transducer elements is used for application of both imaging and therapeutic ultrasound. As another example, a transmitter is provided that transmits therapeutic transmissions having substantially equal positive and negative peaks at the face of the transducer and also is operable to transmit imaging acoustic energy. As yet another example, therapeutic pulses of acoustic energy are transmitted to have greater power for heating than imaging, but a mechanical index or pressure comparable to imaging transmissions. For example, a mechanical index of about 1.9 or lower is provided, such that cavitation of blood or other non-contrast agent is avoided.

26 Claims, 1 Drawing Sheet

ULTRASOUND DRUG DELIVERY ENHANCEMENT AND IMAGING SYSTEMS AND METHODS

BACKGROUND

The present invention relates to ultrasound imaging and therapy. In particular, drug delivery is enhanced through application of ultrasound energy.

In four to six hours after a stroke, physicians attempt to clear the thrombus which caused the stroke. When the thrombus can be cleared within this time frame, patients often recover completely. Typically, an anticoagulant drug is administered to dissolve the thrombus. A thrombus tends to harden over time and may become to stiff for a drug to dissolve. The thrombus may then be removed by the invasive use of a catheter. Catheterizing a patient who recently received an anticoagulant drug is an extremely high risk procedure. Various companies have proposed using ultrasonic energy to assist thrombolysis using high intensity focused ultrasound (HIFU).

A combination of drugs and ultrasound are disclosed in U.S. Pat. Nos. 5,490,840 and 6,165,440. Some chemotherapy drugs are designed to target tumors in response to ultrasound. Ultrasound acoustic energy is applied to cause tissue vibration, heating or cavitation. The tissue vibrations, heating or cavitation release the drug or increase the effectiveness of these chemotherapy drugs while minimizing side effects. In the examples above, a high intensity therapeutic ultrasound transmission device which does not produce images is used. If ultrasonic images are needed, then a second device, dedicated to ultrasonic imaging, is required in addition to the therapeutic device.

In U.S. Pat. No. 5,523,058, Umemura et al. propose an ultrasound system used to create cavitation and for imaging. Cavitation is created through the interaction of transmitted ultrasound energy at a fundamental frequency and a second harmonic of the fundamental frequency. A special transducer is described for this purpose.

BRIEF SUMMARY

The present invention is defined by the following claims, and nothing in this section should be taken as a limitation on those claims. By way of introduction, the preferred embodiments described below include a method and system for both enhancing drug uptake by application of therapeutic transmissions of acoustic energy and imaging a region to help guide the therapy with a same transducer and ultrasound system. An ultrasonic image of a field of view is generated while localized delivery of a drug is enhanced with ultrasound energy. Using the same transducer and ultrasound system reduces costs and increases system availability for a broader range of medical practitioners. For example, a single linear array of transducer elements is used for application of both imaging and therapeutic ultrasound. As another example, a transmitter is provided that transmits therapeutic transmissions having substantially equal positive and negative peaks at the face of the transducer and also is operable to transmit imaging acoustic energy. As yet another example, therapeutic pulses of acoustic energy are transmitted to have greater power for heating than imaging, but a mechanical index or pressure comparable to imaging transmissions. For example, a mechanical index of about 1.9 or lower is provided, such that cavitation of blood or other non-contrast agent is avoided.

Further aspects and advantages of the invention are discussed below in conjunction with preferred embodiments.

BRIEF DESCRIPTION OF SEVERAL VIEWS OF THE DRAWINGS

The components and the Figures are not necessarily to scale, emphasis instead being placed upon illustrating the principles of the preferred embodiment. Moreover, in the Figures, like reference numerals designate corresponding parts throughout the different views.

DETAILED DESCRIPTION OF THE PREFERRED EMBODIMENTS

Figure 1:
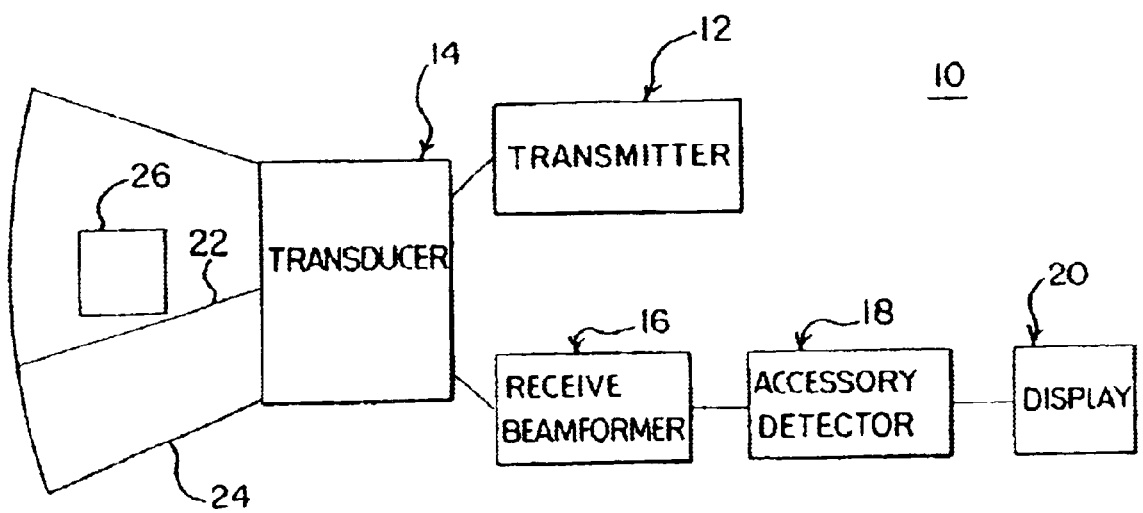
FIG. 1 is a block diagram of one embodiment of an ultrasound system for drug delivery enhancement and imaging.

Localized drug delivery, such as anticancer drug or an anticoagulant drug, is enhanced by therapeutic ultrasound energy, such as energy optimized to heat tissue, move tissue, cause cavitation, or temporarily relax the blood-brain barrier. The ultrasound system responsible for generating the therapeutic ultrasound also generates an image of a tumor, thrombus or other area for drug delivery. The same transmitter and transducer are used for generating B-mode, color Doppler, acoustic radiation force impulse imaging (ARFI), or other imaging and for applying therapeutic acoustic energy. The transmitter and/or transducer transmit both imaging pulses and therapeutic pulses. For example, a single linear transducer array with element spacing designed for imaging is also used for therapeutic ultrasound. As another example, the transducer transmits therapeutic ultrasound energy with substantially equal positive and negative peaks of a multi-cycle waveform. As yet another example, therapeutic ultrasound is transmitted with an energy or power greater than and acoustic pressure substantially similar to imaging transmissions. Substantially similar to includes a same, within a 20% increase or lower.

In one embodiment, a standard ultrasound system, such as the Antares System manufactured by Siemens Medical Solutions USA, Inc. Ultrasound Group or the Sequoia System manufactured by Acuson-A Siemens Company are used with little or no modification. The ultrasound system is capable of generating therapeutic pulses having 50 or more cycles, such as 200 cycles, for each of the channels or transducer elements. Therapeutic transmissions may be repeated 200 times or more along a same scan line or at a same region to move tissue or heat tissue. A trade-off between the number of cycles, the pulse repetition frequency and the transmit amplitude provides the desired heating. For example, fewer cycles with a greater pulse repetition frequency may provide a similar amount of heating as a large number of cycles repeated once. Using a standard or modified transducer, the system also generates images by transmission and reception of acoustic energy. The imaging pulses and therapeutic pulses are interleaved and provided from the same transducer.

By imaging and applying therapeutic ultrasound with the same transducer, more directed application of therapeutic ultrasound is provided. A field of view is imaged and a region of interest within the field of view selected for therapeutic ultrasound. For example, a thrombus or tumor area is identified by imaging. Therapeutic ultrasound energy is then transmitted to heat the region of interest or cause tissue movement within the region of interest. Where drugs have been introduced into a patient, the generation of heat may increase the uptake, release the drug from a protective coating or activate the drug by changing its configuration for localized application of the drug. Tissue movement may increase the uptake of a drug or otherwise release a drug for localized drug delivery enhancement.

FIG. 1 shows an ultrasound system 10 for drug delivery enhancement and imaging using ultrasound energy. The system 10 includes a transmit beamformer 12, a transducer 14, a receive beamformer 16, a processor or detector 18, and a display 20 electrically connected as shown. Additional, different or fewer components may be provided for the system 10. In one embodiment, the system 10 comprises a commercial ultrasound system from one of the manufactures listed above or another manufacturer.

The transducer 14 comprises a piezoelectric or a capacitive microelectromechanical ultrasound transducer. The transducer 14 has one or more elements for transducing between electrical and acoustical energies. In one embodiment, the transducer 14 includes only a single linear array of elements, such as a flat linear array or a curved linear array. In other embodiments, the transducer comprises a two-dimensional array, a 1.5 dimensional array or other multi-dimensional configurations of elements. The array of elements are configured for insertion into a patient or use external to a patient with or without mechanical rotation or position tracking devices.

The transducer 14 is a standard imaging transducer, such as a transducer associated with half wavelength spacing of elements sandwiched between a backing block for absorbing acoustic energy and matching layers for matching the acoustic impedance of the elements to a patient.

In alternative embodiments, a transducer is modified for heat dissipation. For example, a copper foil or copper braid is connected with a lens of the transducer 14 for dissipating heat from the lens. Different piezoelectric materials or matching layers may be optimized for providing a better acoustic or electrical impedance match, reducing an amount of heat generated by the transducer. In one embodiment, multiple layers of piezoelectric or microelectromechanical material separated by electrodes are provided for each element. The multiple layers provide better electrical impedance matching of the transducer to the cable impedance, lowering the generation of heat. In another embodiment, a lensless array or a piezoelectric material shaped to provide elevation focus without a lens focus is provided to reduce the heating of the transducer 14. Reduced heating or more efficient heat dissipation allows for better penetration of acoustic energy and higher power transmissions, such as associated with color Doppler or therapeutic acoustic energy.

The transducer 14 is designed for operation within a frequency band. Typically the frequency band is associated with transmission and reception of both imaging and therapeutic pulses having a same or similar center frequency. In alternative embodiments, the transducer 14 is associated with wide band operation, such as operating to transmit at a fundamental frequency and receive at a second or third order frequency. The imaging and therapeutic pulses may also be provided at substantially different center frequencies, such as associated with a −6 dB down spectral bandwidth that do not overlap.

The transmitter 12 is a transmit beamformer, waveform generator or other source of electrical excitations for imaging and therapeutic transmissions. In one embodiment, the transmitter 12 is a transmit beamformer that generates waveforms for each of a plurality of channels or transducer elements, such as 128 waveforms, separately delayed and apodized for focusing transmissions along scan lines 22 within a field of view 24. Based on the delays and apodization, multiple transmissions may be sequentially scanned across substantially parallel scan lines 22 in the entire field of view 24. The field of view 24 is formed in response to the scan pattern, such as a linear, sector or Vector® scan patterns.

The transmitter 12 includes a large power supply, large capacitors, or other source of energy for generating high power acoustic transmissions. For example, larger capacitors sufficient to provide 50–200 transmit beams of acoustic energy of 50–200 cycles each at a maximum amplitude (e.g. 50–140 volt) with minimal droop or drain are provided. For example, only 10 percent droop allows for ongoing delivery of high power transmit waveforms. Other systems may have different maximum voltages. Alternatively or additionally, an efficient source of ID providing high power transmit waveforms for 50–200 pulses of multiple cycles is provided. Other transmitters 12 capable of other maximum amplitudes, numbers of cycles or numbers of pulses may be used.

The transmitter 12 electrically connects with the transducer 14 for generating transmissions of acoustic energy or transmit pulses in response to the electrical signals from the transmitter 12. The acoustic energy transmitted includes one of imaging or therapy pulses. Imaging pulses are transmissions adapted for generating an image of the field of view 24, such as sequential transmissions of narrow beams sequentially focused along a plurality of scan lines 22. Therapy pulses include transmissions adapted for enhancing drug delivery. Therapy pulses or transmissions are operable to force a change in tissue or fluid, such as forcing movement, changing temperature or causing cavitation. For example, high power pulses adapted to generate heat within a region of interest 26 of the field of view 24 are transmitted. As another example, pulses adapted to cause tissue movement, such as 1–10 microns of tissue movement, for increasing drug uptake or drug release are transmitted. Greater tissue movement, such as associated with cavitation, may be generated by therapeutic transmissions.

The receive beamformer 16 generates receive beams for imaging. The receive beamformer 16 applies various delays and apodization to electrical signals received from elements of the transducer 14 and sums the signals to generate a receive beam representing a scan line 22 in response to each of the transmissions.

The processor or detector 18 comprises one or more of an application specific integrated circuit, general processor, digital signal processor, other digital circuitry, analog circuitry, a combination thereof or other devices for detecting information from the received, beamformed signals for imaging. In one embodiment, the processor 18 comprises a B-mode or Doppler detector. For example, the amplitude of an envelope associated with the received signals is detected. As another example, a frequency shift or velocity, magnitude of a Doppler signal or energy, or variance is detected by Doppler or correlation processing for flow or tissue motion imaging. Other processors for one-dimensional, two-dimensional or three-dimensional imaging may be used.

In one embodiment, tissue movement or ARFI imaging of the field of view 24 is used. For example, U.S. Pat. No. 6,371,912 (application Ser. No. 09/663,271), the disclosure of which is incorporated herein by reference, discloses imaging by causing and detecting tissue motion. The detector or processor 18 detects tissue motion responsive to acoustic transmissions. By causing tissue motion throughout the field of view 24, the relative stiffness or viscosity of tissues is detected.

Prior to causing motion, an imaging pulse of a few cycles, such as 1 to 3 cycles is transmitted along a scan line 22, and receive signals are generated in response to the transmission. For example, a B-mode type pulse at 7.2 MHz with a 0.2 $\mu$sec pulse length, a 5.6 kHz pulse repetition frequency, a derated spatial peak temporal average of less than 0.72 W cm$^{-2}$ and a mechanical index of less than 1.9 (e.g. 0.4). To determine the elasticity or stiffness of tissue, the tissue is then moved away from the transducer 14 with a high power transmission. A high amplitude pushing pulse is transmitted along the scan line 22. For example, transmit beams similar to Doppler imaging beams with longer pulse lengths (e.g. 7.2 MHz, 20 $\mu$sec pulse length, no apodization, F/1.5 focal configuration, 1.2 mechanical index, and a derated spatial peak temporal average intensity approaching 1000 W cm$^{-2}$) are used. In this example, four high amplitude or pushing beams are used for a greater application time (e.g. 4 pulses at a pulse repetition frequency of 5.6 kHz), but fewer, only one or a greater number of such beams may be used. In one embodiment, each pushing pulse or transmit beam has 50 or more, such as 200, cycles at a maximum or high amplitude of the transmitter 12. The acoustic pressure generated by the pulse causes movement of tissue away from the transducer 14, such as 1–10 microns of tissue motion. The transmission of high power acoustic energy to force tissue motion may cause tissue heating, such as 1° C. for a 5 Hertz frame rate.

A second imaging pulse, such as a B-mode imaging pulse, or multiple imaging pulses are transmitted along the same scan line 22. Receive signals are generated in response to the second imaging pulse. The sequence of an imaging pulse, a tissue motion pulse, and an imaging pulse along a scan line 22 is repeated for each of the various scan lines 22 within a field of view 24.

A difference between the receive signals responsive to the two imaging pulses is detected for imaging. The difference is determined as a function of magnitude of tissue movement or speed or response over time of tissue movement. For magnitude, the receive signals of the two imaging pulses along a same scan line 22 are correlated, such as by a cross correlation or other function for determining displacement. The amount of movement of tissue for each or groups of data representing range samples between the first imaging pulse and a second imaging pulse is determined. Stiff tissue is associated with lesser amounts of movement and elastic tissues are associated with greater amounts of movement. A motion filter may be used to remove displacement associated with cardiac and respiratory motion. The detected magnitude of movement is used to generate an image. This acoustic radiation force impulse image is displayed alone or overlaid with a B-mode or Doppler image. Differences in local tissue displacement may indicate a stiffening thrombus or a stiff tumor within more compliant tissue.

Other differences than the magnitude of tissue displacement may be detected for imaging. For example, a temporal response of a tissue forced to move by acoustic energy is detected. Fatty tissue is more compliant and tends to take longer to recover then other tissues (i.e. more viscous). Muscle or other stiff tissues may tend to move back to an original position more quickly. By transmitting multiple imaging pulses after a tissue movement pushing pulse, the response of the tissue position over time is determined by correlation. These differences in the envelope of displacement response of the tissue are detected and imaged. For example, any of displacement as a function of time, a recovery velocity (e.g. the slope of the displacement time curve from a peak displacement to recovery of the original position), the time to reach peak displacement or the maximum displacement are detected and used for imaging.

A two-dimensional image is generated using any of the B-mode, Doppler or acoustic radiation force impulse imaging methods discussed above. The detected information from the processor 18 is provided to the display 20. An image representative of the imaging pulses is generated on the display. Various combinations or single types of images are displayed substantially simultaneously, such as one or more of a B-mode, Doppler or acoustic radiation force impulse image. In one embodiment, portions of a field of view 24, such as lateral edges, are shown as B-mode or Doppler images, and another portion, such as a laterally centered portion, is displayed as an acoustic radiation force impulse image. The spacing of scan lines associated with an acoustic radiation force impulse image may be different than associated with B-mode or Doppler imaging. For example, 10 to 30 scan lines through a center of an image spaced 0.2 millimeters apart are transmitted for acoustic radiation force impulse imaging. These transmissions and associated receptions are interleaved with transmission and reception of imaging pulses for B-mode image at the edges of the field of view 24. Like B-mode imaging, detected magnitude or temporal information for acoustic radiation force impulse imaging is displayed as an image at a particular time even though the scan line information is acquired sequentially. In one embodiment, five frames of information are acquired for each second, but greater or lesser frame rates may be provided. A sequence of images, such as associated with 10 milliseconds of imaging, may be stored and repetitively generated on the display 20. Such a sequence may represent 10 to 20 frames of information. Other information may be displayed, such as a graph of mean displacement by axial position as a function of time along one or more scan lines 22.

Using the system 10 described above, a field of view is imaged. A suspected thrombus, tumor or other region of interest is identified on the image by the user. In one embodiment, acoustic radiation force impulse imaging is used to better identify a stiffening thrombus or a stiff tumor. The same system 10, including the same transmitter 12 and transducer 14, are then used to transmit therapeutic pulses. For example, therapeutic transmissions are used to vibrate a thrombus to increase drug penetration or uptake. The therapeutic transmissions may also increase the temperature of the selected region of interest, causing a temperature-sensitive drug to be locally activated, or causing cavitation of contrast agents or fluid for drug release, or destroying contrast agents or other structures containing drugs to release the drugs within the selected region of interest. By applying a therapeutic transmission to a selected region of interest smaller than the field of view 24, undesired side effects of drugs in other regions are minimized. An ultrasound system designed to support acoustic radiation force impulse imaging and/or B-mode or Doppler imaging may also provide therapeutic ultrasound energy to enhance the effectiveness of drugs. By combining the imaging and therapeutic functions in a single device, time critical procedures are expedited. For example the success rate of application of an anticoagulant drug is increased, reducing the number of catheterizations of a thrombus required. Using a same system for both imaging and therapy also reduces the cost associated with extra equipment.

Figure 2:
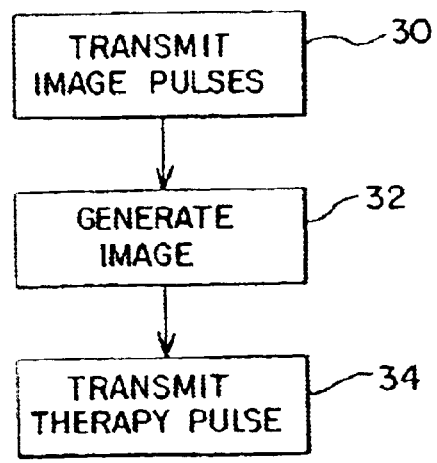
FIG. 2 is a flow chart diagram of one embodiment for drug delivery enhancement and imaging.

FIG. 2 shows the acts of an ultrasound method for drug delivery enhancement and imaging. Imaging pulses are transmitted in act 30. In act 32, an image is generated in response to the imaging pulses. In the act 34, therapy pulses are transmitted. Additional or different acts may be provided.

In act 30, any of various imaging pulses are transmitted. For example, pulses for B-mode or Doppler imaging are transmitted. For B-mode imaging, a 1–5 cycle pulse is transmitted along each of the scan lines within the field of view 24. For Doppler imaging, a plurality of transmit pulses for determining a Doppler coefficient, correlation or flow characteristic are transmitted along each scan line. Other imaging pulses are possible, such as pulses for acoustic radiation force impulse imaging discussed above. The transmit pulses have a transmit power determined from the number of cycles, amplitude and pulse repetition frequency of the transmit pulses. The transmit pulse pressure is limited by the Food and Drug Administration to particular mechanical indexes within the field of view. Typically, ultrasound systems provide a transmit pressure near the maximum mechanical index.

In response to the imaging pulses, an image of a field of view is generated in act 32. The field of view is determined by the position of the transducer 14, the steering of the imaging transmissions and the selected depths of viewing. The field of view 24 is optimized to view a potential region of interest and surrounding tissue. In response to a single image or a sequential set of images, a user selects a region of interest 26 within the field of view 24. Alternatively, the system 10 automatically determines the region of interest 26 within the field of view 24. The region of interest 26 is associated with a region for application of therapy transmissions. For example, the tumor associated with stiff tissue movement or increased blood flow or a thrombus associated with stiff tissue movement is identified within the image. A portion of a tumor or thrombus is selected, or the entire thrombus or tumor is selected.

In act 34, a therapy pulse is transmitted. The therapy pulse is adapted to cause a change in tissue or fluid. For example, acoustic energy causes tissue to heat within a localized area, such as the region of interest. As another example, the therapy transmission causes tissue to oscillate, repetitively move or move to increase drug uptake for destruction of tissue. As yet another example, acoustic energy causes cavitation for increasing drug uptake. The therapy pulse has an acoustic power greater than the imaging pulses. The greater power causes a greater affect on tissue.

Greater power is provided by increasing the number of cycles, increasing the transmit amplitude, increasing the pulse repetition frequency or combinations of those. In one embodiment, the therapy transmission includes multiple cycles and more than one transmission to a same area. For example, a waveform with 50 or more, such as 200 cycles, is transmitted repetitively, such as 50–200 transmit beams, to a same focal region. In one embodiment, heat is generated in tissue by transmitting a 50 cycle waveform at a 10 kHz pulse repetition frequency for a few minutes to an hour or more. Other combinations of fewer or more cycles with lesser or more pulse repetitions, at an imaging, lesser or greater pressure amplitude may be used. For example, a single cycle waveform with a pulse repetition frequency of 200 KHz is used at an imaging waveform amplitude.

The focal region is selected to be within the region of interest 26. Various delays and apodizations may be provided for increasing the acoustic power applied within the region of interest 26 and minimizing the acoustic power applied outside the region of interest 26.

In one embodiment, the therapy pulses are associated with a single frequency band, such as the same frequency band used for imaging or another frequency band. Only one peak is provided for the spectral response within a six dB down band of frequencies from the maximum amplitude. Substantially equal positive and negative amplitudes of the transmitted acoustic energy waveform are provided. For multiple cycle waveforms, the substantial equal positive and negative peaks provide a narrow band pulse. In alternative embodiments, multiple frequency bands, wide band or waveforms with other characteristics are provided.

Therapy transmissions provide a maximum acoustic energy at the focal zone of the transmitted beam. The transmit energy is greater than the transmit energy caused by imaging pulses. The energy may be the same or greater than the energy provided by the acoustic radiation force impulse imaging. Due to repetition, an increased power is provided for therapy by application of the same energy as for imaging. In one embodiment, the transmit pressure and associated power is operable to heat tissue by 3° C. or more, such as 3–6°, but less or more of an increase may be provided. By transmitting for longer periods of time, such as minutes or even an hour or more, heat improves delivery of drugs, depending on the characteristics of the drug. In another embodiment, transmit pressure is applied to cause focused tissue movement of 15 to 100 microns, such as for displacing a Thrombus. To avoid extra or minimize additional hardware for the transmitter 12, therapeutic pulses of acoustic energy are transmitted to have greater power for heating, but a mechanical index or pressure comparable to imaging transmissions. For example, a mechanical index of about 1.9 or lower is provided, such that cavitation of blood or other non-contrast agent is avoided. Greater or lesser transmit pressures may be provided.

In one embodiment, fewer than all of the elements of an array, such as a sparsely spaced 8 or more elements are used for the therapy transmissions. By using fewer elements, less power is required from the system. Breast tissue or other absorbing tissue allows a comparable pressure, such as within a factor of two, at a focal region with a large reduction in the number of elements used as compared to using all of the elements. In other embodiments, all of or a large number of elements are used.

Therapy pulses may be interleaved with imaging pulses. Interleaving allows substantially continuous imaging while therapy pulses are transmitted. The user is better able to maintain the proper position of the transducer 14 relative to the tissue for the application of the therapy pulses. The system 10 may also automatically track the region of interest 26 as a function of the identified tissue and adjust the focal position of the therapy pulses.

The imaging system 10 and the same transducer 14 provide acoustic output for imaging and to enhance drug delivery or therapy. Any of various imaging methods are used to identify a region of interest. Therapeutic ultrasound is then focused within the localized region of interest. The focused therapy transmissions cause vibration, heating, or cavitation (e.g. destruction of contrast agent) for enhanced drug delivery or other therapeutic effects. By localizing the application of the therapeutic transmissions, the drugs are most effective where needed, minimizing drug dosages or side effects outside of the region of interest. In one application, a fresh thrombus in a stroke victim is cleared. Anticoagulation drugs are injected within the patient. Tissue motion responsive to acoustic radiation force is detected to identify the thrombus. Focused therapy pulses are transmitted to the thrombus to encourage penetration of the anticoagulation drug and disrupt the thrombus. This procedure is performed with the same system and even with interleaved imaging to better satisfy the time critical requirements for dissolving a thrombus. As another example application, a tumor is identified within an image. The chemotherapy or other drug is injected into the patient. Therapy transmissions then increase the uptake or performance of the drug within the region of interest, such as the tumor. In one embodiment, the chemotherapy drug is a polypeptide that undergoes a phase transition from soluble to insoluble as a function of temperature. Therapy pulses increase the temperature within the region of interest by 3 degrees or more, causing the drug to interact with the tumor. Where drugs have a strong side effect in other areas of the body, such focused or localized application of ultrasound avoids many of the side effects.

The therapy transmissions may provide therapeutic effects without drugs. Alternatively, drugs assist in the therapy or the effectiveness of drugs is increased by the therapy. The drug may be injected or provided to the patient with or without an additional delivery mechanism. For example, drugs are provided to a patient free of contrast agents or microsphere containers. Contrast agents typically comprise microbubbles that burst upon application of high power ultrasound. Focusing high power ultrasound at just one region allows for localized delivery of drugs by bursting the contrast agents. Localized effectiveness of drugs may be increased without use of contrast agents by moving tissue or heating tissue.

While the invention has been described above by reference to various embodiments, it should be understood that many changes and modifications can be made without departing from the scope of the invention. It is therefore intended that the foregoing detailed description be understood as an illustration of the presently preferred embodiments of the invention, and not as a definition of the invention. It is only the following claims, including all equivalents, that are intended to define the scope of this invention.

What is claimed is:

1. An ultrasound system for drug delivery enhancement and imaging, the system comprising:
   a transducer having only one linear array of elements;
   a transmitter connected with the transducer, the transmitter operable to both generate an imaging transmission of acoustic energy from the linear array and to generate a therapy transmission of acoustic energy from the linear array; and
   a display operable to display an image representative of the imaging transmission.

2. The system of claim 1 wherein the transmitter is operable to generate the therapy transmission having substantially equal positive and negative peaks at a face of the transducer.

3. The system of claim 1 wherein the transmitter is operable to generate the therapy transmission with a single frequency band.

4. The system of claim 1 wherein the transmitter is operable to generate the therapy transmission having a power greater than the imaging transmission and a pressure substantially similar to the imaging transmission.

5. The system of claim 1 wherein the transmitter is operable to generate the therapy transmission as a pulse of about 50 or more cycles.

6. The system of claim 1 wherein the transmitter is operable to generate the imaging transmission as a plurality of beams; and further comprising:
   a processor operable to determine a difference in response to the plurality of beams, the difference associated with tissue movement;
   wherein the image is representative of the difference.

7. The system of claim 1 wherein the transmitter is operable to generate the imaging transmission over a field of view and the therapy transmission at a region of interest smaller than the field of view.

8. An ultrasound method for drug delivery enhancement and imaging, the method comprising the acts of:
   (a) transmitting imaging pulses of acoustic energy from a transducer having only one linear array of elements;
   (b) generating an image in response to (a); and
   (c) transmitting a therapy pulse of acoustic energy from the transducer.

9. The method of claim 8 wherein (c) comprises transmitting the therapy pulse having substantially equal positive and negative peaks at a face of the transducer.

10. The method of claim 8 wherein (a) and (c) comprise transmitting the therapy transmission having a power greater than the imaging transmission and a pressure substantially similar to the imaging transmission.

11. The method of claim 8 wherein (c) comprises transmitting the therapy pulse with about 50 or more cycles.

12. The method of claim 8 wherein (a) comprises transmitting a plurality of beams along a same scan line; and further comprising:
   (d) determining a difference in response to the plurality of beams of (a), the difference associated with tissue movement;
   wherein the image is representative of the difference.

13. The method of claim 8 wherein (a) comprises transmitting the imaging pulses over a field of view and (c) comprises transmitting the therapy pulses at a region of interest smaller than the field of view.

14. An ultrasound system for drug delivery enhancement and imaging, the system comprising:
   a transducer;
   a transmitter connected with the transducer, the transmitter operable to both generate an imaging transmission of acoustic energy and to generate a therapy transmission of acoustic energy, the therapy transmission having substantially equal positive and negative peaks at a face of the transducer; and
   a display operable to display an image representative of the imaging transmission.

15. The system of claim 14 wherein the transmitter is operable to generate the therapy transmission having a power greater than the imaging transmission and a pressure substantially similar to the imaging transmission.

16. The system of claim 14 wherein the transmitter is operable to generate the therapy transmission as a pulse of about 50 or more cycles.

17. The system of claim 14 wherein the transmitter is operable to generate the imaging transmission as a plurality of beams; and further comprising:
   a processor operable to determine a difference in response to the plurality of beams, the difference associated with tissue movement;
   wherein the image is representative of the difference.

18. The system of claim 14 wherein the transmitter is operable to generate the imaging transmission over a field of view and the therapy transmission at a region of interest smaller than the field of view.

19. The system of claim 14 wherein the transducer comprises a multi-dimensional array of elements.

20. An ultrasound method for drug delivery enhancement and imaging, the method comprising the acts of:
   (a) transmitting imaging pulses of acoustic energy from a transducer;

(b) generating an image in response to (a); and (c) transmitting a therapy pulse of acoustic energy from the transducer, the therapy pulse having substantially equal positive and negative peaks at a face of the transducer.

21. The system of claim 20 wherein (a) and (c) comprise transmitting the therapy transmission having a power greater than the imaging transmission and a pressure substantially similar to the imaging transmission.

22. The method of claim 20 wherein (c) comprises transmitting the therapy pulse with about 50 or more cycles.

23. The method of claim 20 wherein (a) comprises transmitting a plurality of beams along a same scan line; and further comprising:

(d) determining a difference in response to the plurality of beams of (a), the difference associated with tissue movement;

wherein the image is responsive to the difference.

24. The method of claim 19 wherein (a) comprises transmitting the imaging pulses over a field of view and (c) comprises transmitting the therapy pulses at a region of interest smaller than the field of view.

25. The method of claim 20 wherein (a) comprises transmitting from a multi-dimensional array of elements.

26. An ultrasound method for drug delivery enhancement and imaging, the method comprising the acts of:

(a) transmitting imaging pulses of acoustic energy from a transducer;

(b) generating an image in response to (a); and (c) transmitting a therapy pulse of acoustic energy from the transducer, the therapy pulses having a power greater than the imaging transmission and the therapy pulses having a pressure substantially similar to the imaging transmission.

* * * * *